United States Patent [19]

Brown et al.

[11] 4,117,140
[45] Sep. 26, 1978

[54] BRONCHODILATING PIPERIDINOETHYL BENZOPYRANOPYRIDINONES

[76] Inventors: Richard E. Brown, 16 Ridge Dr., East Hanover, N.J. 07936; Chester Puchalski, 9 Locust Ave., Dover, N.J. 07801; John Shavel, Jr., Yardley Pl., Mendham, N.J. 07945

[21] Appl. No.: 811,818

[22] Filed: Jun. 30, 1977

Related U.S. Application Data

[63] Continuation-in-part of Ser. No. 743,839, Nov. 22, 1976, which is a continuation-in-part of Ser. No. 548,298, Feb. 10, 1975, abandoned.

[51] Int. Cl.$^2$ .............................................. C07D 491/04
[52] U.S. Cl. ............................... 424/267; 260/293.51; 260/293.58; 260/293.86; 260/293.88
[58] Field of Search .................... 260/293.58; 424/267

[56] References Cited

U.S. PATENT DOCUMENTS 4,018,766  4/1977  Brown et al. ................... 260/293.58

OTHER PUBLICATIONS

Chemical Abstracts, 82, 4302N (1975) [German Offen. 2,411,847, Brown et al, 10/10/74], Abstract Date 1/6/75.

Primary Examiner—Henry R. Jiles
Assistant Examiner—Richard A. Schwartz
Attorney, Agent, or Firm—Albert H. Graddis; Frank S. Chow; George M. Yahwak

[57] ABSTRACT

Disclosed are novel substituted benzopyranopyridines which are active as bronchodilators.

6 Claims, No Drawings

BRONCHODILATING PIPERIDINOETHYL BENZOPYRANOPYRIDINONES

This application is a continuation-in-part of our application Serial No. 743,839, filed 22 November 1976, the disclosure of which is hereby incorporated by reference, which in turn is a continuation-in-part of our application Ser. No. 548,298, filed 10 February 1975 and now abandoned, the disclosure of which is hereby incorporated by reference.

This invention relates to novel substituted benzopyranopyridines of the formula I.

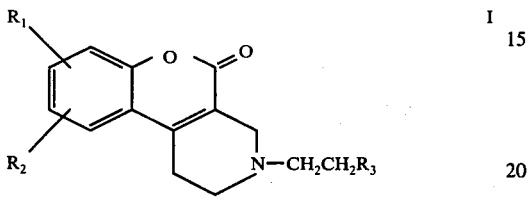

In the above formula, $R_1$ and $R_2$ may be hydrogen, hydroxy, lower alkoxy or lower alkyl of 1 to 6 carbon atoms or may be taken together to form a methylenedioxy group. $R_3$ is a substituted piperidine ring selected from the class including the following partial formulae:

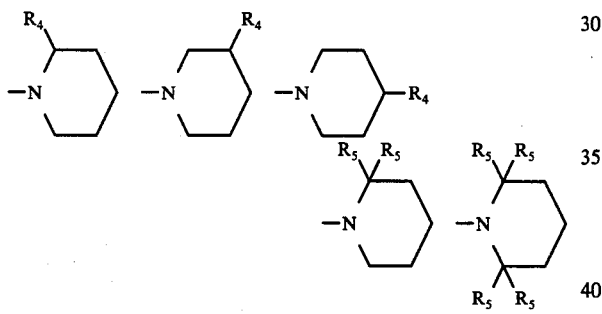

In the above partial formulae, $R_4$ may be a lower alkyl group of 1 to 6 carbon atoms, an aralkyl group of 1 to 6 carbon atoms in the chain or a carboxy group or ester or amide derivative thereof of the formula

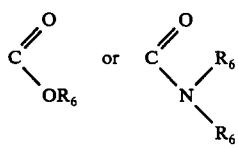

in which $R_6$ may be hydrogen or a lower alkyl group of 1 to 6 carbon atoms. $R_5$ may be a lower alkyl group of 1 to 6 carbon atoms.

The compounds of this invention are prepared by reacting a substituted benzopyranopyridine of structure II with a suitable alkylating agent selected from the group represented by structures III to VII. The starting materials according to structure II are described in our U.S. Pat. No. 3,946,008. The alkylating agents of structures III to VII are known compounds and are either commercially available or are prepared by methods standard to the art.

In structure II to VII, $R_1$, $R_2$, $R_4$ and $R_5$ are as defined for formula I. Hal. refers to halogen and may be chlorine, bromine or iodine.

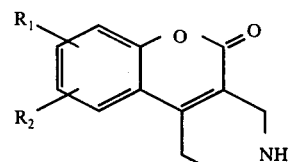

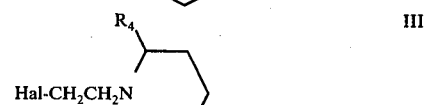

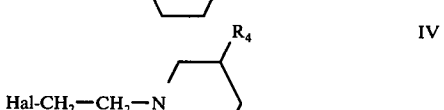

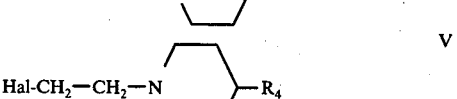

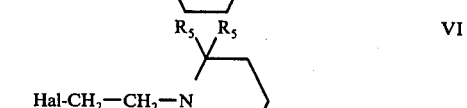

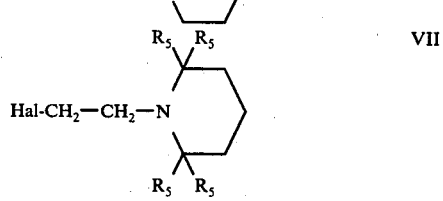

The alkylation reactions are carried out in a suitable solvent in the presence of a base to serve as proton acceptor. Among the solvents which may be used are alcohols of 1 to 6 carbon atoms such as methanol, ethanol or amyl alcohol; polar aprotic solvents as dimethylformamide, dimethylsulfoxide and the like, tetrahydrofuran and dioxane. Suitable bases are potassium carbonate, sodium acetate or triethylamine.

The following examples are given in order to further illustrate the inventions:

EXAMPLE 1

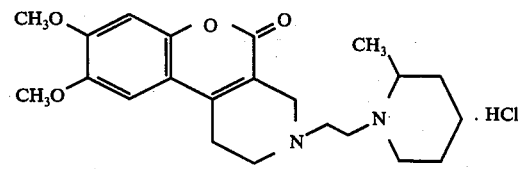

1,2,3,4-Tetrahydro-8,9-dimethoxy-3-[2-(2-methylpiperidino)ethyl]-5H-[1]benzopyrano[3,4-c]pyridin-5-one hydrochloride. A solution of 0.03m of 1,2,3,4-tetrahydro-8,9-dimethoxy-5H-[1]benzopyrano[3,4-c]pyridin-5-one, 0.035m of 1-(2-chloroethyl)-2-methylpiperidine.HCl, and 0.07m of triethylamine in 125ml of EtOH was refluxed for 17 hours, treated with an additional 0.005m of 1-(2-chloroethyl)-2-methylpiperidine.HCl, and heated for 7 additional hours. After standing overnight, the precipitate was filtered off and crystallized twice from 95% EtOH affording 3.2g of material, m.p. 209°-12° C.

Anal. Calcd. for C₂₂H₃₀N₂O₄.HCl: C, 62.48; H, 7.39; N, 6.62; Cl, 8.38. Found: C, 62.07; H, 7.39; N, 6.62; Cl, 8.39.

EXAMPLE 2

N-(2-Hydroxyethyl)-4-benzylpiperidine. A solution of 0.2m of 4-benzylpiperidine in 100ml of EtOH was treated with a stream of 0.39m of ethylene oxide in 45 minutes. The reaction was refluxed for 1 hour and evaporated in vacuo. Distillation of the residue afforded 32g of material, B.P. 123°–36°/0.05–0.01mm.

Anal. Calcd. for C₁₄H₂₁NO: C, 76.66; H, 9.65; N, 6.39. Found: C, 76.60; H, 9.76; N, 6.66.

EXAMPLE 3

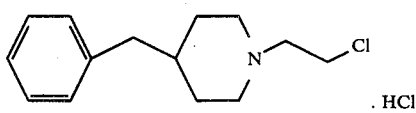

N-(2-Chloroethyl)-4-benzylpiperidine hydrochloride. A solution of 0.046m of N-(2-hydroxyethyl)-4-benzylpiperidine in 100ml of CHCl₃ was treated with 0.1m SOCl₂ and refluxed for 3 hours. After evaporation, the residue was crystallized from CH₃CN affording 6.5g of material, m.p. 229°–31° C.

Anal. Calcd. for C₁₄H₂₀ClN HCl: C, 61.32; H, 7.72; N, 5.11; Cl, 25.86. Found: C, 61.61; H, 7.80; N, 5.16; Cl, 25.78.

EXAMPLE 4

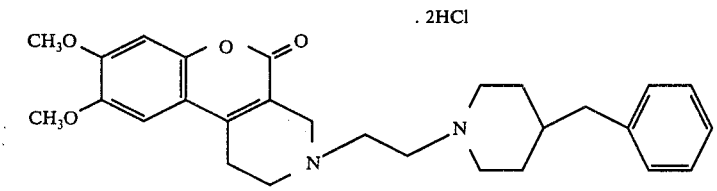

3-[2-(4-benzylpiperidino)ethyl]1,2,3,4-tetrahydro-8,9-dimethoxy-5H-[1]benzopyrano[3,4-c]pyridin-5-one dihydrochloride. In a manner similar to example 1, 0.02m of 1,2,3,4-tetrahydro-8,9-dimethoxy-5H-[1]benzopyrano [3,4-c]pyridin-5-one was alkylated with 0.022m of 1-(2-chloroethyl)-4-benzylpiperidine HCl to give, after crystallization from MeOH, 5.0g of material, mp 240°–3° C.

Anal. Calcd. for C₂₈H₃₄N₂O₄ 2HCl: C, 62.80; H, 6.78; N, 5.23; Cl, 13.24. Found: C, 62.29; H, 6.75; N, 5.19; Cl, 13.34.

EXAMPLE 5

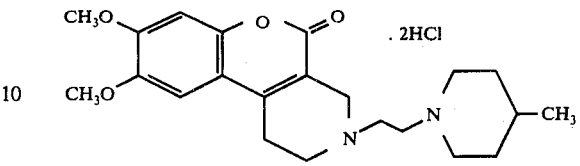

1,2,3,4-Tetrahydro-8,9-dimethoxy-3-[2-(4-methylpiperidino)ethyl]-5H-[1]benzopyrano[3,4-c]pyridin-5-one dihydrochloride. In a manner similar to example 1, 0.02m of 1,2,3,4-tetrahydro-8,9-dimethoxy-5H-[1]benzopyrano[3,4-c]pyridin-5-one was alkylated with N-[2-chloroethyl]-4-methylpiperidine HCl. Recrystallization from MeOH afforded 3.3g of material, m.p. 253°–7° C.

Anal. Calcd. for C₂₂H₃₀N₂O₄ 2HCl: C, 57.52; H, 7.02; N, 6.10; Cl, 15.43. Found: C, 57.67; H, 7.16; N, 5.93; Cl, 15.29.

EXAMPLE 6

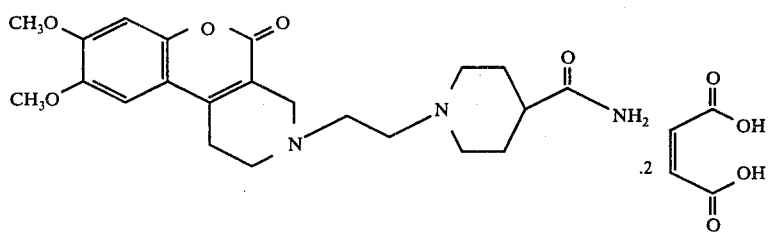

1-[2-(1,2,3,4-Tetrahydro-8,9-dimethoxy-5-oxo-5H-[1]benzopyrano [3,4-c]pyridin-3-yl)ethyl]-4-piperidinecarboxamide dimaleate. A solution of 0.2m of isonipecotamide in 100ml of EtOH was treated with 0.66m of ethylene oxide in 1 hour. The mixture was refluxed for 1 hour, and was then evaporated in vacuo. Without purification, a suspension of 0.08m of crude N-(hydroxyethyl)isonipecotamide and 100ml of CHCl₃ was stirred, treated with 0.13m of SOCl₂, and refluxed for 4 hours. After evaporation, the crude salt was treated with 0.04m of 1,2,3,4-tetrahydro-8,9-dimethoxy-5H-[1]benzopyrano [3,4-c]pyridin-5-one, 0.2m of triethylamine, and 250ml of EtOH, and was refluxed for 24 hours. The reaction was evaporated in vacuo. The residue was dissolved in 100ml of water, made strongly basic by addition of conc. NH₄OH, and was extracted with CHCl₃. The CHCl₃ solution was dried (Na₂SO₄), and evaporated. The residue was crystallized from 300ml of CH₃CN affording 2.6g of crude base. A suspension of 2.4g of base in 100ml of acetone was treated with 1g of maleic acid in 50ml of acetone, and was stirred overnight. Filtration afforded 2.8g of dimaleic acid salt, m.p. 90°–109° C.

Anal. Calcd. for $C_{22}H_{29}N_3O_5 \cdot 2C_4H_4O_4$: C, 55.64; H, 5.76; N, 6.49. Found: C, 55.34; H, 5.85; N, 6.51.

EXAMPLE 7

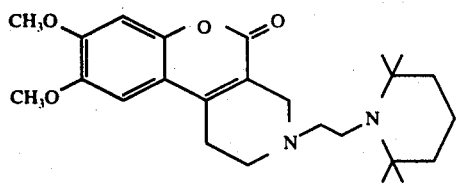

1,2,3,4-Tetrahydro-8,9-dimethoxy-3-[2-(2,2,6,6-tetramethylpiperidino)ethyl]-5H-1-benzopyrano[3,4-c]pyridin-5-one. A solution of 0.02m of 1,2,3,4-tetrahydro-8,9-dimethoxy-5H-[1]benzopyrano[3,4-c]pyridin-5-one, 0.0246m of 1-(2-chloroethyl)-2,2,6,6-tetramethylpiperidine hydrochloride*, and 0.05m of triethylamine in 125ml of EtOH was refluxed for 20 hours, treated with an additional 0.0083m of 1-(2-chloroethyl)-2,2,6,6-tetramethylpiperidine HCl and 0.02m of triethylamine, and was refluxed for an additional 23 hours. After evaporation, the residue was partitioned between dil. $NH_4OH$ soln. and $CHCl_3$. $CHCl_3$ soluble material was recovered and crystallized twice from MeOH affording 4.3g of product, m.p. 154°–6° C.

* Robertson, J. E., et al. J. Med. Chem., 6 (4) 381 (1963).

Anal. Calcd. for $C_{25}H_{36}N_2O_4$: C, 70.06; H, 8.47; N, 6.54. Found: C, 70.13; H, 8.44; N, 6.80.

EXAMPLE 8

| TEST ANIMAL: | Male albino guinea pigs (250–350 gm) | | |
|---|---|---|---|
| ROUTE OF ADMINISTRATION: | Intraperitoneal | | |
| DOSES: | 25 mg/kg | | |
| SPASMOGENS: | Acetylcholine chloride | 0.3% | |
| | Histamine | 0.1% | (most frequently |
| | Methacholine chloride (Mecholyl) | 0.1% | used) |
| | Serotonin creatinine sulfate | 1.25% | |
| PROCEDURE: | Pigs are continuously exposed to a spasmogen for 10 min.; delivery is by means of two nebulizers (Each nebulizer dispenses 0.2 cc/min.) positioned at the back of a closed, six unit plexiglas chamber (19 × 12½ × 9 in.) and driven by an air pressure of 10 lbs/in². The time from onset of the aerosol treatment to collapse of each animal is recorded; mean values for drug treated animals are compared to those of animals treated with vehicle. Guinea pigs that do not collapse during the 10 min. period are removed from the chamber and a maximum score of 10 is recorded. Test compounds (25 mg/kg, i.p.) are given 15 min. before exposure to spasmogen. | | |

(See Siegmund, O.H. et al: J. Pharmacol and Exptl. Therapeutics, 90:254, 1949)

Following the protocol of Example 8, a series of tests were performed in which the compounds of the examples were compared to animals receiving only the spasmogen, histamine. The results obtained are given in the following table:

TABLE I

| Dose | Animals | Collapse Time |
|---|---|---|
| Control | 3 | 1.8 |
| 25 mg (Example 1) | 3 | 8.2 |
| Control | 3 | 1.9 |
| 25 mg (Example 4) | 3 | 10.0 |
| Control | 3 | 1.9 |
| 25 mg (Example 5) | 3 | 10.0 |
| Control | 3 | 2.3 |
| 25 mg (Example 6) | 3 | 10.0 |

In each instance, and under identical test situations, the compounds of the present invention showed a marked ability to protect the animals from bronchial spasms.

The compounds of this invention are active as a bronchodilator for all spasmogens listed in Example 8, and protects the guinea pig against bronchospasm for a duration up to 4 hours at an oral dose of 10 mg/kg. Thus, it is more effective against bronchospasm than aminophylline, a commercial product used in the treatment of bronchial asthma and pulmonary edema, which protects the guinea pig against identical bronchospasm for less than two hours at a dose of 100 mg/kg. In addition, the compounds disclosed in this invention reverse pilocarpine or histamine bronchconstriction in the dog for a duration of up to 1 hour at an oral dose of 10 mg/kg. The bronchodilator activity exhibited by the N-substituted benzopyrano[3,4-c]pyridines described in this invention is the result of a direct smooth muscle relaxant effect on the bronchial tree as shown by in vitro experiments on guinea pig trachea. In these experiments, the N-substituted benzopyrano[3,4-c] pyridines are approximately 75 times more active than aminophylline in relaxing tracheal smooth muscle.

The compounds of this invention are useful for the treatment of bronchial asthma. Generally speaking, a dose of about 500 mg to 1000 mg several times daily is recommended for mammals weighing about 70 kilograms. The compounds can be administered orally or by parenteral administration.

In order to use these compounds they are formulated with pharmaceutically acceptable excipients such as lactose, starch, powdered sugar and the dosage forms can be tablets, capsules and the like. The dosage regimen can be varied according to the condition being treated by methods well known to the healing arts.

We claim:

1. A compound of the formula:

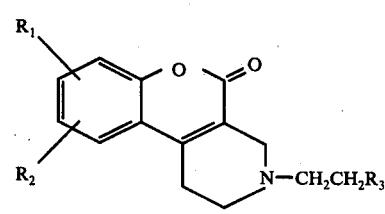

wherein $R_1$ and $R_2$ are selected from the group consisting of hydrogen, hydroxy, lower alkoxy or alkyl of 1 to 6 carbon atoms, or taken together $R_1$ and $R_2$ is a methylenedioxy group, and wherein $R_3$ is selected from the group consisting of:

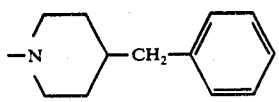

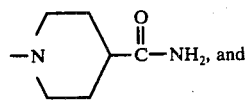

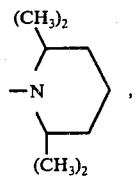

and the pharmaceutical acceptable salts thereof.

2. A compound according to claim 1 wherein $R_1$ and $R_2$ are methoxy.

3. 3-[2-(4-benzylpiperidino)ethyl]1,2,3,4-tetrahydro-8,9-dimethoxy-5H-[1]benzopyrano[3,4-c]pyridin-5-one.

4. 1-[2-(1,2,3,4-tetrahydro-8,9-dimethoxy-5-oxo-5H-[1]benzopyrano [3,4-c]pyridin-3-yl)ethyl]-4-piperidine-carboxamide dimaleate.

5. 1,2,3,4-tetrahydro-8,9-dimethoxy-3-[2-(2,2,6,6-tetramethylpiperidino)ethyl]-5H-1-benzopyrano[3,4-c]pyridin-5-one.

6. A method of producing bronchodilation in a mammal which comprises the administration of an effective bronchodilating amount of a compound selected from the group consisting of 3-[2-(4-benzylpiperidino)ethyl]1,2,3,4-tetrahydro-8,9-dimethoxy-5H-[1]benzopyrano[3,4-c]pyridin-5-one and 1-[2-(1,2,3,4-tetrahydro-8,9-dimethoxy-5oxo-5H-[1]benzopyrano[3,4-c]pyridin-3-yl)ethyl]-4-piperidine-carboxamide dimaleate to said mammal.

* * * * *